US010463532B2

(12) United States Patent
Murata

(10) Patent No.: US 10,463,532 B2
(45) Date of Patent: Nov. 5, 2019

(54) METHOD FOR PLACING IMPLANT IN CHOROID THAT CAN LESS INVASIVELY AND SIMPLY PLACE IMPLANT IN CHOROID IN OPTIC DISC-MACULA AREA

(71) Applicant: Masatoshi Murata, Morioka (JP)

(72) Inventor: Masatoshi Murata, Morioka (JP)

(*) Notice: Subject to any disclaimer, the term of this patent is extended or adjusted under 35 U.S.C. 154(b) by 387 days.

(21) Appl. No.: 15/219,823

(22) Filed: Jul. 26, 2016

(65) Prior Publication Data
US 2018/0028356 A1 Feb. 1, 2018

(51) Int. Cl.
*A61F 9/00* (2006.01)
*A61F 9/007* (2006.01)

(52) U.S. Cl.
CPC ........ *A61F 9/0017* (2013.01); *A61F 9/00736* (2013.01); *A61F 2250/0067* (2013.01)

(58) Field of Classification Search
CPC ............ A61F 2250/0067; A61F 9/0017; A61F 9/00736; A61M 5/3286
See application file for complete search history.

(56) References Cited

U.S. PATENT DOCUMENTS

| | | | |
|---|---|---|---|
| 5,164,188 A | 11/1992 | Wong | |
| 6,514,238 B1 * | 2/2003 | Hughes | A61F 2/14 604/239 |
| 6,936,053 B1 * | 8/2005 | Weiss | A61F 9/0017 604/117 |
| 8,349,005 B2 | 1/2013 | Murata | |
| 9,216,107 B2 | 12/2015 | Silvestrini et al. | |
| 2002/0198511 A1 | 12/2002 | Varner et al. | |
| 2009/0017097 A1 * | 1/2009 | Sawhney | A61K 9/0051 424/427 |
| 2014/0221904 A1 * | 8/2014 | Murata | A61K 31/573 604/20 |
| 2015/0065940 A1 | 3/2015 | Rangel-Friedman et al. | |

OTHER PUBLICATIONS

Beeley, N. et al., "Fabrication, implantation, elution, and retrieval of a steroid-loaded polycaprolactone subretinal implant," J Biomed Mater Res A., 2005, p. 437-44, vol. 73, No. 4, Wiley Periodicals, Inc.
Humayun, M. et al., "Implantable MicroPump for Drug Delivery in Patients with Diabetic Macular Edema," TVST, 2014, p. 1-8, vol. 3, No. 6, Article 5.

* cited by examiner

*Primary Examiner* — Brandy S Lee
(74) *Attorney, Agent, or Firm* — Manabu Kanesaka

(57) ABSTRACT

An implant is placed in the choroid in the posterior eye segment. The conjunctiva is incised, and an injection needle is inserted between the conjunctiva and the sclera. The tip of the injection needle is advanced to the vicinity of the optic disc along the surface of the sclera. After placing a vitrectomy lens over the cornea so that the eyeground can be observed, the tip of the injection needle that appears white is observed while observing the eyeground through the vitrectomy lens and pressing the sclera using the injection needle. The injection needle is moved to determine an appropriate insertion position of the implant in the vicinity of the optic disc, and is inserted diagonally into the sclera. The tip of the injection needle is advanced into the choroid, and the implant is inserted into the choroid through the tip opening formed at the tip of the injection needle.

6 Claims, 14 Drawing Sheets
(5 of 14 Drawing Sheet(s) Filed in Color)

METHOD FOR PLACING IMPLANT IN CHOROID THAT CAN LESS INVASIVELY AND SIMPLY PLACE IMPLANT IN CHOROID IN OPTIC DISC-MACULA AREA

TECHNICAL FIELD

The invention relates to an eye treatment method. In particular, the invention relates to a method for placing an implant in the choroid that is effective for the treatment of posterior segment eye diseases (particularly retinal or choroidal diseases in an area from the optic disc to the macula) that are responsible for the loss of sight, and a tool that makes it possible to less invasively and simply place an implant in the choroid.

BACKGROUND ART

Posterior segment inflammatory diseases and proliferative diseases (e.g., uveitis, diabetic retinopathy, proliferative vitreoretinopathy, and macular degeneration) are serious diseases that require long-term medication.

Dexamethasone (DEX) and other anti-inflammatory drugs, antibiotics, antibodies, and the like are commonly used to treat posterior segment eye diseases. Posterior segment eye diseases normally require long-term administration of such a drug. However, it is difficult to continuously deliver the effective dose of drug to the posterior eye segment for a long time.

Specifically, systemic administration requires administration of a large dose of drug, and may cause a complication such as hypertension. Eye drops penetrate poorly into the posterior eye segment due to corneal impermeability and the like. Intravitreal injections must be repeated to maintain the effective (therapeutic) level, and involve the potential risk of serious complications such as infections.

A method that implants a drug in the vitreous body (intravitreal implant) is known as a method that can solve these problems, and it has been reported that the intravitreal implant is effective to treat posterior segment eye diseases. However, since the intravitreal implant requires intraocular surgery, infections and the like may occur (i.e., the eye may be significantly affected) in the same manner as in the case of using intravitreal injections.

Periocular drug delivery (e.g., a method that implants a drug in the sclera (intrascleral implant)) is also known as a method for delivering a drug to the posterior eye segment in a sustained manner. This method is safer than the intravitreal implant, but has a problem in that the drug does not sufficiently reach the retina. This is because the drug must pass through a barrier such as the sclera, the choroid, and the retinal pigment epithelium in order to reach the retina, and is eliminated from ocular tissue through the scleral and choroidal blood flows.

The inventor developed technology that implants a drug in the choroid (intrachoroidal implant) (that had been considered to be impossible), and a method for adjusting the drug release level from an intrachoroidal implant, and reported that the intrachoroidal implant is effective for delivering a drug to the posterior eye segment in a sustained manner (see U.S. Pat. No. 8,349,005 and US-A-2014/0221904).

The choroid is situated between the sclera and the retina. Since the retina is an important tissue that includes photoreceptor cells, bipolar cells, ganglion cells, Müller cells, and the like, it is necessary to pay careful attention so as not to damage the retina when performing choroidal surgery. However, since the human choroid is a thin membrane having a thickness of about 0.3 mm, and the intraocular pressure is applied to the choroid in the outward direction, it is very difficult to perform surgery that forms an implant insertion pocket in the choroid without damaging the retina.

The inventor succeeded in placing an implant in the choroid by liquefying the vitreous gel in the eyeball, exposing the choroid, aspirating the vitreous humor to decrease the intravitreous pressure (intraocular pressure), incising the choroid in the tangential direction, expanding the choroid through bleeding to form a space, and forming a pocket in the choroid.

According to this method, since it is unnecessary to perform intraocular surgery, it is possible to ensure safety as compared with the intravitreal implant. Moreover, since the implant is situated close to the retina, the drug easily reaches the retina as compared with the intrascleral implant.

SUMMARY OF THE INVENTION

Posterior segment eye diseases that occur in an area from the optic disc to the macula are normally serious and responsible for loss of sight. Therefore, it is effective to inject a drug solution into an area in the vicinity of the optic disc in order to treat serious eye diseases such as macular degeneration since the optic disc is situated close to the macula.

The above method that implements the intrachoroidal implant merely enables the placement of the implant in the equatorial choroid that is situated relatively away from the optic disc (see FIG. 10), and has an advantage in that the drug easily reaches the retina as compared with the intrascleral implant. However, it makes more sense to bring the position of the intrachoroidal implant closer to the optic disc. Specifically, since an intrachoroidal implant placed in the vicinity of the optic disc can deliver a drug to an area from the optic disc to the macula (i.e., an area in which serious diseases responsible for loss of sight normally occur) at the effective dose, a higher effect can be obtained. This has been expected by researchers in the ophthalmological field, but technology that can implement such an improvement has not yet been established.

U.S. Pat. No. 5,164,188 discloses a biodegradable ocular implant as related eye treatment technology, for example. According to the technology disclosed in U.S. Pat. No. 5,164,188, since the implant (suprachoroidal implant) is placed between the sclera and the choroid, the drug reaches the retina to a small extent as compared with the intrachoroidal implant, and it is difficult to place the implant in the vicinity of the optic disc.

U.S. Pat. No. 9,216,107 and US-A-2015/0065940 also disclose a suprachoroidal implant. According to the technology disclosed in U.S. Pat. No. 9,216,107 and US-A-2015/0065940, however, it is impossible to place the implant in the vicinity of the optic disc.

A method that places an implant under the retina is also known (see J Biomed Mater Res A 2005, pp. 437-444 Fabrication, implantation and retrieval of a subretinal implant). However, this method has a problem in that surgery takes time and is highly invasive.

A method that treats the retina using a tube as an implant is known (see tvst 2014, pp. 1167-1174, Implantable Micro-Pump for Drug Delivery in Patients with Diabetic Macular Edema). According to this method, the implant is placed in the vitreous body at pars plana to treat the retina, and the drug can be released in a sustained manner using a pump.

However, this method has a problem in that the drug does not sufficiently reach the vicinity of the optic disc.

US-A-2002/0198511A1 discloses a method and a device for subretinal drug delivery. According to the technology disclosed in US-A-2002/0198511A1, a tube is inserted under the retina through the vitreous body to deliver a drug to the retina and the choroid. However, this technology does not release the drug in a sustained manner, is highly invasive, and may cause infections and the like. Moreover, surgery takes time, and the eye may be significantly affected.

In view of the above situation, the inventor conducted further extensive studies, and developed a novel method for placing an implant in the choroid that can less invasively and simply place an implant in the choroid in the vicinity of the optic disc to complete the invention.

Specifically, an object of the invention is to provide a method for placing an implant in the choroid that can place an implant in the choroid in the vicinity of the optic disc within a short time, and rarely causes serious complications such as infections, and a tool for placing an implant in the choroid.

A method for placing an implant in the choroid according to the invention that achieves the above object includes incising the conjunctiva, inserting an injection needle between the conjunctiva and the sclera, advancing the tip of the injection needle to the vicinity of the optic disc along the surface of the sclera, placing a vitrectomy lens over the cornea so that the eyeground can be observed, observing the tip of the injection needle that is seen as an elevated white area in the sclera while observing the eyeground through the vitrectomy lens and pressing the sclera using the tip of the injection needle, moving the tip of the injection needle to determine an appropriate insertion position of the implant in the vicinity of the optic disc, inserting the tip of the injection needle diagonally into the sclera, advancing the tip of the injection needle into the choroid, and inserting the implant into the choroid through the tip opening formed at the tip of the injection needle.

A tool for placing an implant in the choroid according to the invention is used to place the implant when implementing the method for placing an implant in the choroid, and includes:

an injection needle that includes a main body that includes a tip having a tip opening at one end, and is hollow and curved, and a support that supports the main body; and a plunger that is inserted into the main body, and pushes the implant forward through the tip opening.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DESCRIPTION OF EMBODIMENTS

A method for placing an implant in the choroid according to the exemplary embodiments of the invention is described in detail below with reference to the drawings. The structure of the eye is described below with reference to FIG. 1.

Structures of Eye

Figure 1:
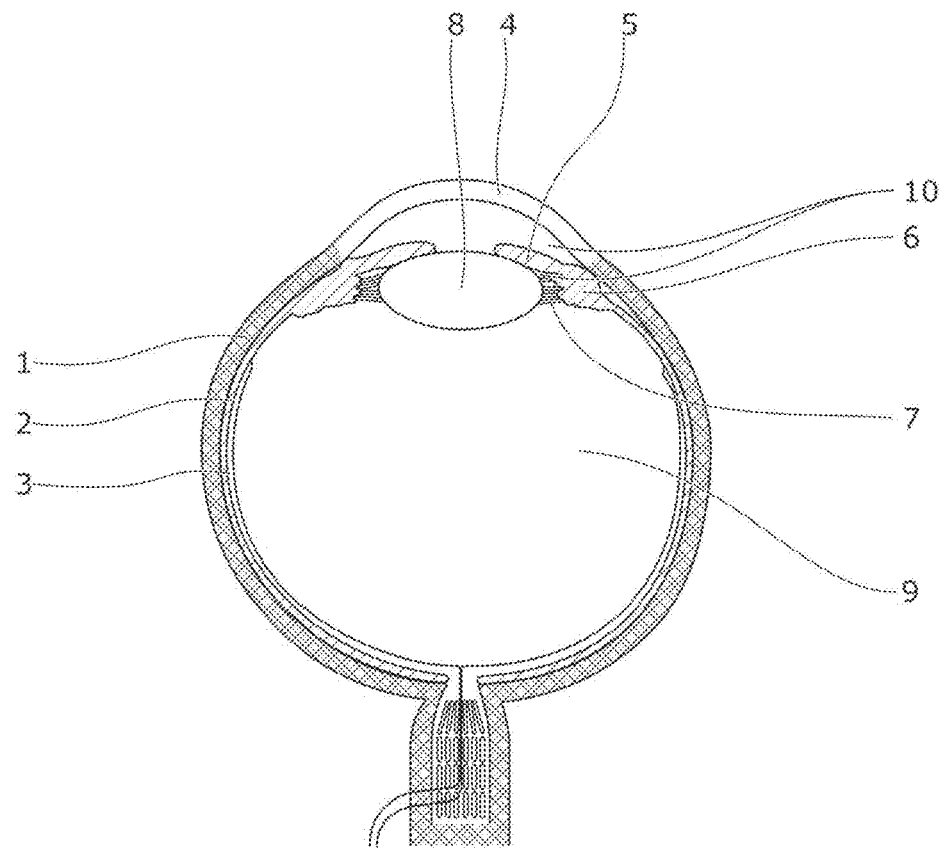
FIG. 1 is a view illustrating the structure of an eye.

An eye includes an eyeball, adnexa, and optic nerves. As illustrated in FIG. 1, the eyeball includes outer wall members such as a sclera 1, a choroid 2, a retina 3, a cornea 4, an iris 5, a ciliary body 6, and a zonule of Zinn 7, and content members such as a crystalline lens 8, a vitreous body 9, and an aqueous humor 10. The adnexa include a lacrimal apparatus, a conjunctiva, and the like. The outer wall of the posterior eye segment has a three-layer structure in which the sclera 1 forms an outer layer, the choroid 2 forms an intermediate layer, and the retina 3 forms an inner layer. Although FIG. 1 illustrates the structure of the human eye, the target for which the implant is placed in the choroid 2 using the method according to the invention is not limited to a human. The method according to the invention may also be applied to various animals (e.g., rabbit, monkey, dog, cat, horse, and cow) having an eyeball structure similar to that of a human.

The sclera 1 is a milky white hard membrane. The end of the sclera 1 is connected to the cornea. The sclera 1 allows light to pass through to only a small extent, and prevents the entry of unnecessary light into the eyeball. The sclera 1 thus protects the inside of the eyeball. The sclera 1 has a thickness of about 1.0 mm to about 1.5 mm in an area in which the sclera 1 forms the rear wall of the eyeball, and has a minimum thickness of about 0.5 mm in an area in which the eye muscle adheres to the sclera 1.

The choroid 2 is a thin blackish brown membrane that is situated between the sclera 1 (that is situated on the outer side) and the retina 3 (that is situated on the inner side). A number of blood vessels are present in the choroid 2, and supply nutrients to the outer layer of the retina in which blood vessels are not present. The thickness of the choroid 2 is about 0.2 mm to about 0.3 mm.

The retina 3 is a thin membrane that includes ten layers. The retina 3 has a thickness of about 0.3 mm to about 0.4 mm in the center area, and has a thickness of about 0.15 mm in the peripheral area. Two types of photoreceptor cells (rod cells and cones) are present in the retina 3. Important cells such as ganglion cells and Müller cells and a number of blood vessels are also present in the retina 3. A macular area in which a number of cones are present is situated at the center of the rear part of the retina 3. The macular area is part of the eyeball that has the best visual acuity.

The vitreous body 9 is a colorless and transparent gel with which most of the interior of the eyeball is filled. Water accounts for 99% of the vitreous body 9. The vitreous body 9 is situated behind the crystalline lens. The vitreous body 9 is bonded to the retina 3 in a deep area of the eyeball, but most of the vitreous body 9 comes in light contact with the retina 3.

Macular degeneration is a serious disease that occurs in the macular area of the retina 3. Macular edema (due to diabetes or retinal hemorrhage) and the like also occur in the macular area of the retina 3. The macular area has a visual function significantly better than that of the remaining part of the retina 3, and is a key area for achieving vision. Macular degeneration is characterized in that bleeding, exudation (exudate), and the like occur in the macular area, and symptoms such as reduced visual acuity and metamorphopsia are observed. One type of macular degeneration is characterized in that an abnormal blood vessel (that is referred to as a neovascularization and is not present in a healthy state) is formed from the choroid 2, and extends toward the retina 3. Since the wall of the neovascularization is very fragile, bleeding, exudation (exudate), and the like occur in the macular area.

Bruch's membrane is present between the choroid 2 and the retina 3, and the loss of visual acuity does not occur when the neovascularization is situated under the Bruch's membrane. However, when the neovascularization has broken through the Bruch's membrane, and reached a position under or over the pigment epithelium of the retina 3, the growth of the neovascularization is suddenly promoted, and exudation of blood occurs to a large extent, whereby a significant loss of visual acuity occurs. In particular, it is difficult to effectively treat macular degeneration when a neovascularization has reached the central pit.

A method that inserts an implant that releases a drug in a sustained manner into the sclera 1 or the vitreous body 9 (corpus ciliare) may be used to treat diseases that occur in the choroid 2 and the retina 3.

It is considered that it is preferable to insert an implant into the choroid 2 instead of the sclera 1 or the vitreous body 9 (corpus ciliare) since the distance from the implant to the diseased part decreases, so that a high therapeutic effect can be obtained, and the dosage can be reduced.

However, surgery that places an implant in the choroid 2 is very difficult as compared with surgery that places an implant in the sclera 1 or in the vitreous body at pars plana, and technology that makes it possible to implement surgery that places an implant in the choroid 2 was reported for the first time by the inventor (see U.S. Pat. No. 8,349,005).

The inventor has developed a novel method for placing an implant in the choroid in the vicinity of the optic disc within a short time, and rarely causes serious complications such as infections (see below).

Method for Placing Implant in Choroid

The method for placing an implant in the choroid according to the embodiments of the invention is described below with reference to FIGS. 2 to 9. FIGS. 2 to 9 illustrate a state in which an injection needle is inserted diagonally downward with respect to a plane. Note that the side of the three-layer structure of the outer wall of the posterior eye segment that is contiguous to the vitreous body 9 is referred to as "upper side", and the side of the three-layer structure that is formed by the sclera 1 is referred to as "lower side" for convenience of explanation.

Although the embodiments and the examples described below illustrate an example in which the method for placing an implant in the choroid is implemented on a rabbit, the invention can also be applied to a human. The invention is not limited to the embodiments and the examples described below as long as the method according to the invention includes incising the conjunctiva, inserting an injection needle between the conjunctiva and the sclera, advancing the tip of the injection needle to the vicinity of the optic disc along the surface of the sclera, placing a vitrectomy lens over the cornea so that the eyeground can be observed, observing the tip of the injection needle that is seen as an elevated white area in the sclera while observing the eyeground through the vitrectomy lens and pressing the sclera using the tip of the injection needle, determining the appropriate insertion position of the implant in the vicinity of the optic disc, inserting the tip of the injection needle diagonally into the sclera, advancing the tip of the injection needle into the choroid, and inserting the implant into the choroid through the tip opening formed at the tip of the injection needle.

(1) Injection Needle Insertion Step

Figure 2:
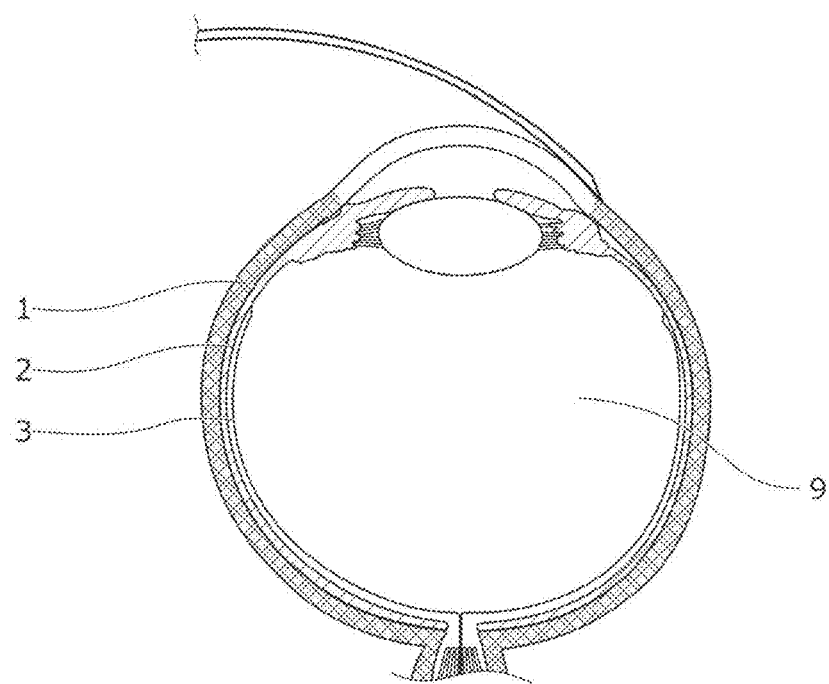
FIG. 2 is a schematic view illustrating a state in which the conjunctiva is incised, and an injection needle is inserted between the conjunctiva and the sclera when implementing the method for placing an implant in the choroid according to the embodiments of the invention (the conjunctiva is omitted (hereinafter the same (e.g., FIGS. 3, 4, and 9))).
Figure 3:
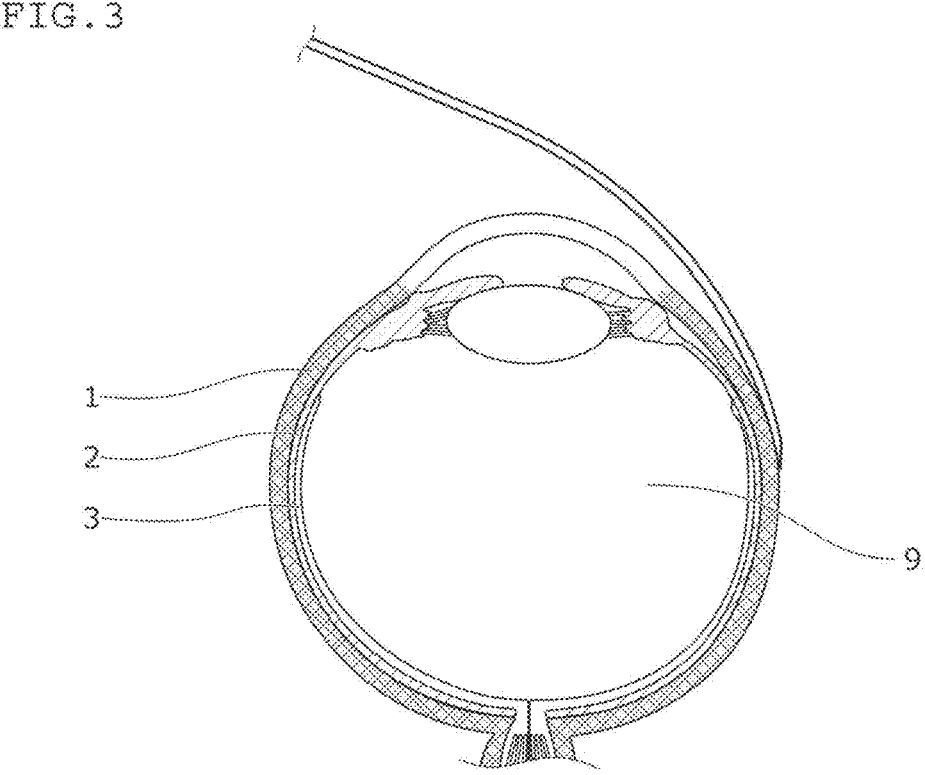
FIG. 3 is a schematic view illustrating a state in which the tip of an injection needle is advanced along the surface of the sclera when implementing the method for placing an implant in the choroid according to the embodiments of the invention.

As illustrated in FIGS. 2 and 3, the conjunctiva that covers the eyeball of the subject is incised, and an injection needle is inserted between the conjunctiva and the sclera. An example in which a white domestic rabbit is used as the subject is described below. A white domestic rabbit is easily available, has an eyeball having a structure similar to that of a human eyeball, and can also be used as an eyeball disease model animal.

As illustrated in FIGS. 2 and 3, an injection needle in which the main body is gently curved may suitably be used as the injection needle. When the main body of the injection needle is curved in this manner, the injection needle can be inserted between the conjunctiva and the sclera, and the tip of the injection needle can be moved to the vicinity of the optic disc. It is preferable that the injection needle have a size as small as possible from the viewpoint of invasiveness. Note that it may be difficult to provide an implant if the size of the injection needle is too small. It is preferable that the injection needle have a size of 24G or 25G from this point of view. It is more preferable if an injection needle having a smaller size can be used.

A plunger is inserted into the injection needle together with an implant, and the plunger is moved forward inside the injection needle to push the implant into tissue through the tip of the injection needle. The plunger may be moved manually by pressing the rear end of the plunger with the finger, for example. The plunger may also be moved using an injector. For example, a pen-type electric dispenser manufactured by ICOMES LAB Co. Ltd. may suitably be used as the injector. This dispenser is a pipette that can discharge a trace amount (e.g., 0.1 µL) of liquid (world's most accurate pipette at present).

Figure 13B:
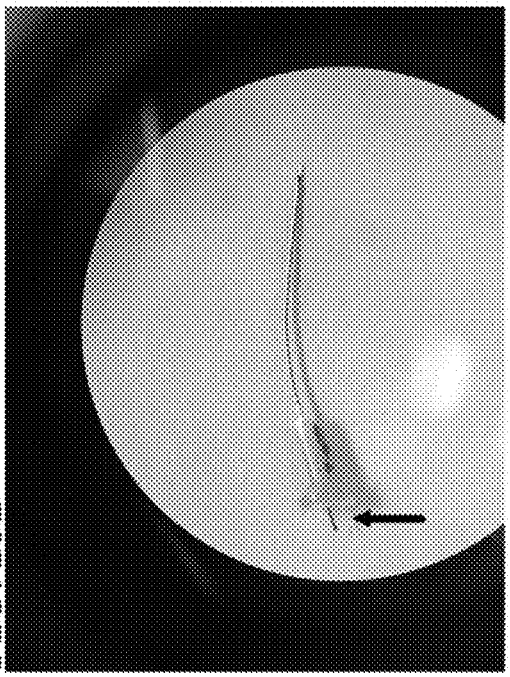
FIG. 13B is a view illustrating an injection needle used when implementing the method for placing an implant in the choroid according to the embodiments of the invention.
Figure 13D:
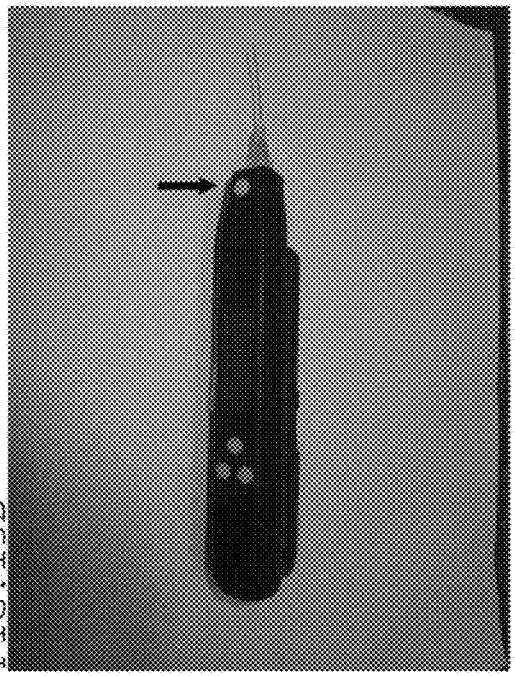
FIG. 13D is a view illustrating an injector that gradually moves a plunger inside an injection needle.
Figure 13A:
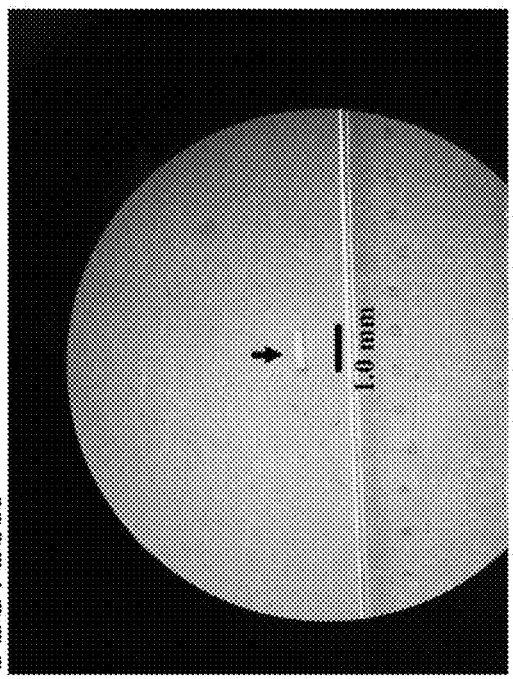
FIG. 13A is a view illustrating an implant used when implementing the method for placing an implant in the choroid according to the embodiments of the invention.
Figure 13C:
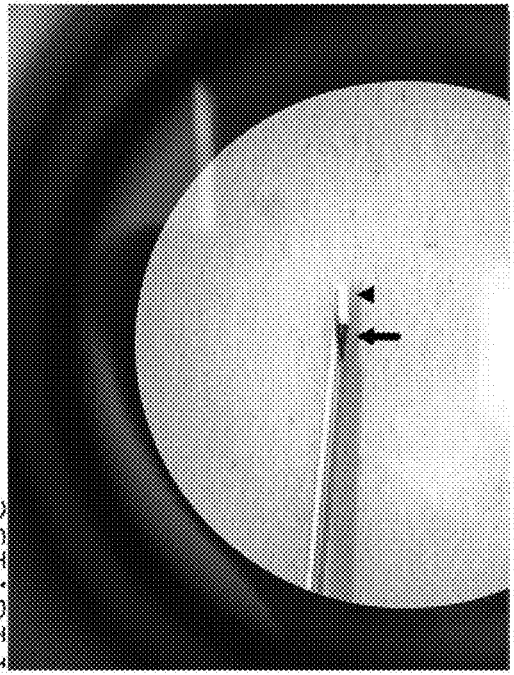
FIG. 13C is a view illustrating a state in which an implant is pushed forward by a plunger through the tip of an injection needle.

Note that FIG. 13A illustrates an implant used when implementing the method for placing an implant in the choroid according to the embodiments of the invention, FIG. 13B illustrates an injection needle used when implementing the method for placing an implant in the choroid according to the embodiments of the invention, FIG. 13C illustrates a state in which the implant is pushed forward by the plunger through the tip of the injection needle, and FIG. 13D illustrates an injector that gradually moves the plunger inside the injection needle.

(2) Implant Position Determination Step

Figure 4:
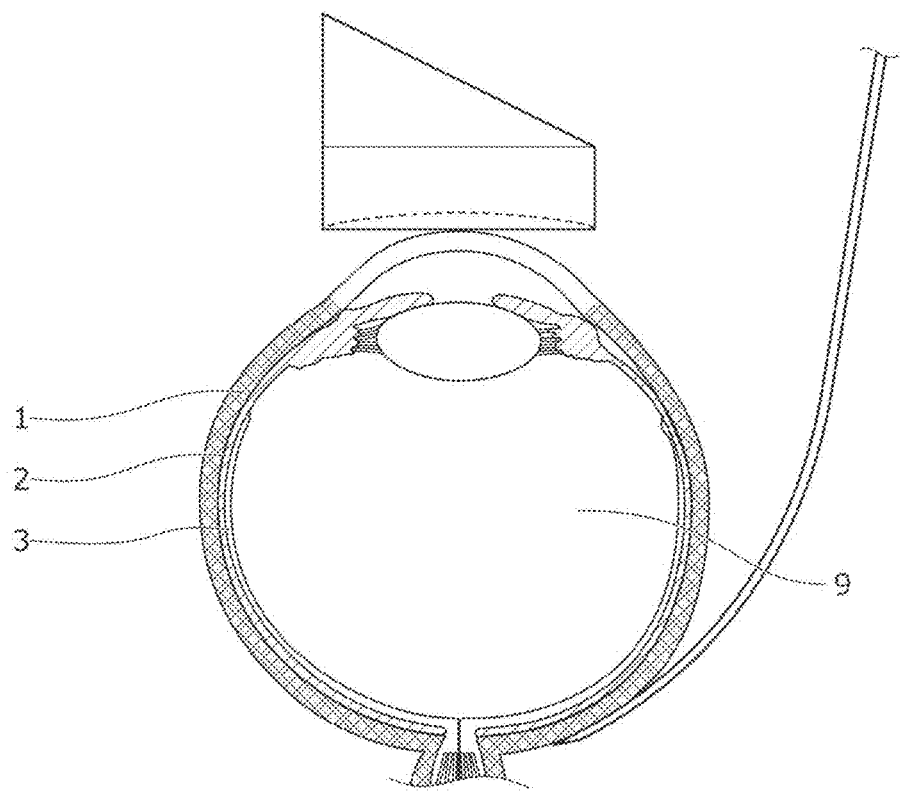
FIG. 4 is a schematic view illustrating a state in which the tip of an injection needle has been advanced to the vicinity of the optic disc along the surface of the sclera, and a vitrectomy lens has been placed over the cornea so that the eyeground can be observed, when implementing the method for placing an implant in the choroid according to the embodiments of the invention.

As illustrated in FIG. 4, the tip of the injection needle is advanced to the vicinity of the optic disc along the surface of the sclera. A vitrectomy lens is placed over the cornea so that the eyeground can be observed, and the tip of the injection needle that is seen as an elevated white area in the sclera is observed through the vitrectomy lens while pressing the sclera using the tip of the injection needle to determine the appropriate insertion position of the implant.

In this case, the state of the sclera is observed through the vitrectomy lens while pressing the sclera using the tip of the injection needle, and the surface of the sclera that is contiguous to an area of the choroid in the vicinity of the optic disc in which the number of blood vessels is small and a large vessel is not present, is determined to be the appropriate insertion position of the implant.

(3) Step that Inserts Injection Needle into Choroid

Figure 5:
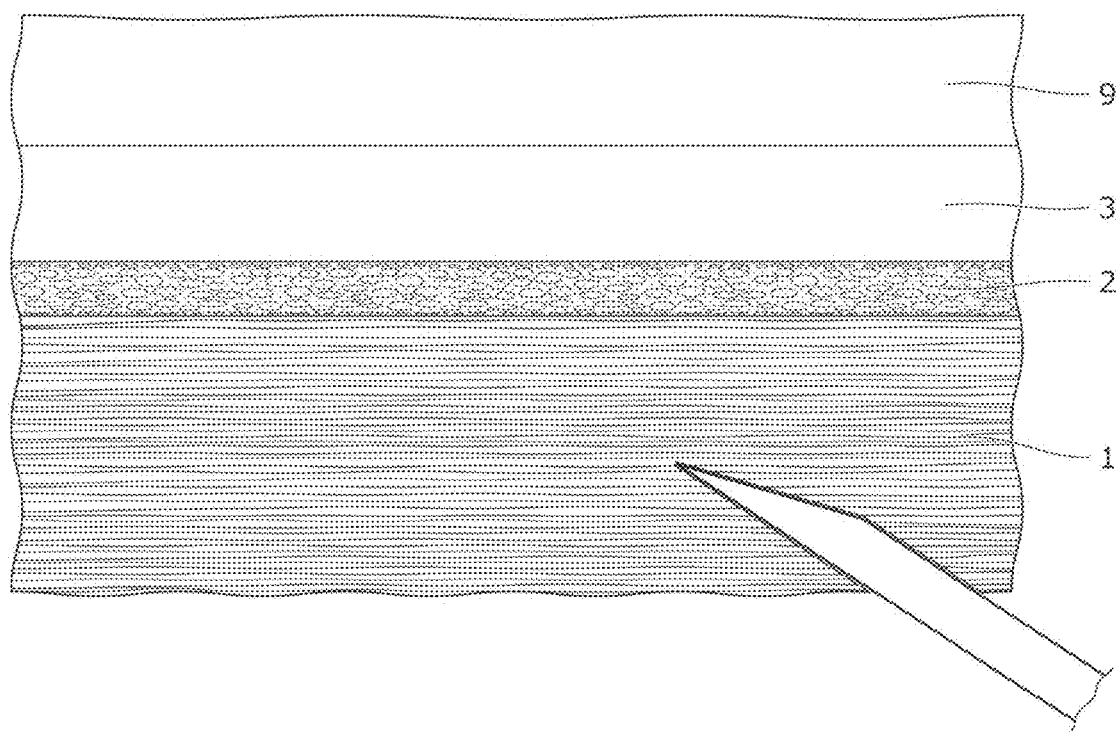
FIG. 5 is an enlarged schematic view illustrating a state in which the tip of an injection needle has been diagonally inserted into the sclera when implementing the method for placing an implant in the choroid according to the embodiments of the invention.
Figure 6:
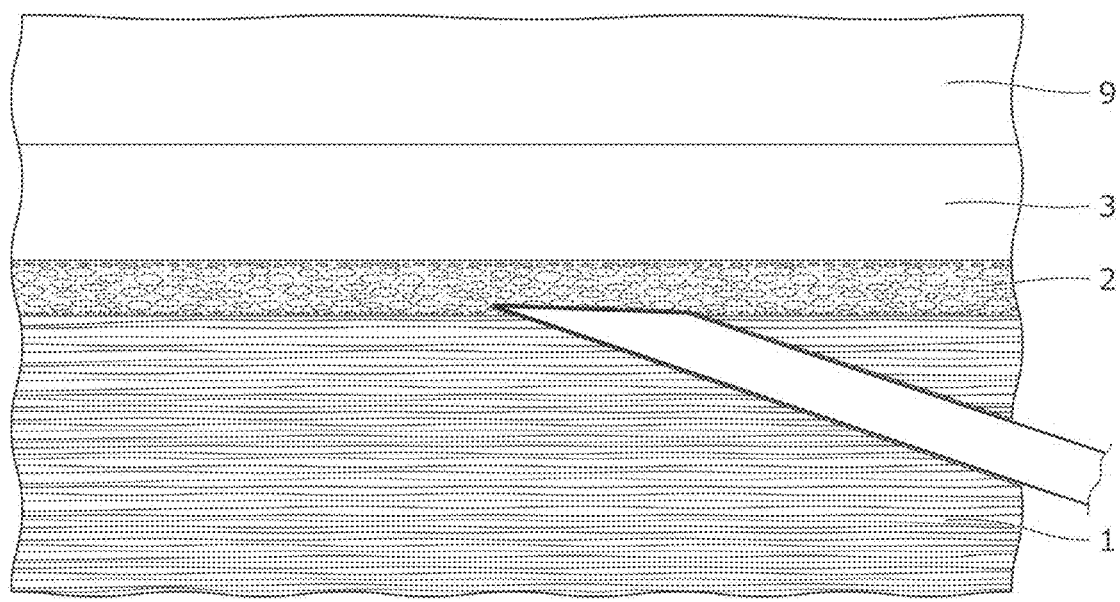
FIG. 6 is an enlarged schematic view illustrating a state in which the tip of an injection needle is diagonally inserted into the choroid when implementing the method for placing an implant in the choroid according to the embodiments of the invention.
Figure 7:
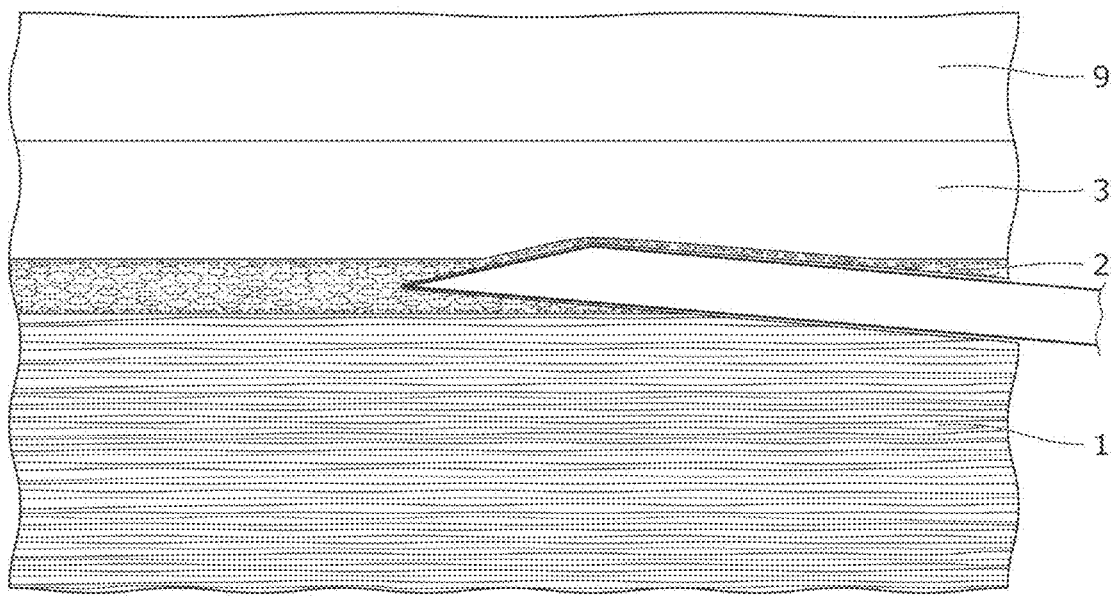
FIG. 7 is an enlarged schematic view illustrating a state in which the tip of an injection needle is advanced within the choroid parallel to the choroid when implementing the method for placing an implant in the choroid according to the embodiments of the invention.

As illustrated in FIG. 5, the tip of the injection needle is diagonally inserted into the sclera. As illustrated in FIGS. 6 and 7, the tip of the injection needle is then advanced into the choroid.

The tip of the injection needle has been inserted into the choroid is determined while observing the eyeground through the vitrectomy lens.

Specifically, it is determined that the tip of the injection needle has been inserted into the choroid when a state in which the tip of the injection needle is observed through a thick membrane comprising the retina, the choroid, and the sclera (i.e., an area of the sclera pressed by the tip of the injection needle is observed to be a white area) has changed to a state in which the tip of the injection needle is observed through a thin membrane comprising the retina and the choroid (i.e., the tip of the injection needle is clearly observed under the retina having a small thickness) when observed through the vitrectomy lens.

Specifically, since the sclera allows light to pass through to only a small extent, the tip of the injection needle is situated under or within the sclera in a state in which the tip of the injection needle is observed through a thick membrane. On the other hand, the tip of the injection needle is situated under the retina and over the sclera in a state in which the tip of the injection needle is observed through a thin membrane. Therefore, it can be determined that the tip of the injection needle has been inserted into the choroid when the tip of the injection needle is observed through a thin membrane.

When the tip of the injection needle has been inserted into the choroid, the tip of the injection needle is advanced within the choroid parallel to the choroid. Specifically, the tip of the injection needle is moved parallel to (in the tangential direction with respect to) the layer that forms the choroid.

The tip of the injection needle is advanced within the choroid parallel to the choroid until it is observed through the vitrectomy lens that the tip opening of the injection needle has been inserted into the choroid. It is determined that the tip opening of the injection needle has been inserted into the choroid when the tip opening of the injection needle can be observed through a thin membrane.

Note that the method that determines that the tip of the injection needle has been inserted into the choroid when a state in which the tip of the injection needle is observed through a thick membrane has changed to a state in which the tip of the injection needle is observed through a thin membrane when the eyeground is observed through a vitrectomy lens, and the method that determines that the tip opening of the injection needle has been inserted into the choroid when the tip opening of the injection needle can be observed through a thin membrane when the eyeground is observed through a vitrectomy lens, are novel methods developed by the inventor.

(4) Implant Placement Step

Figure 8:
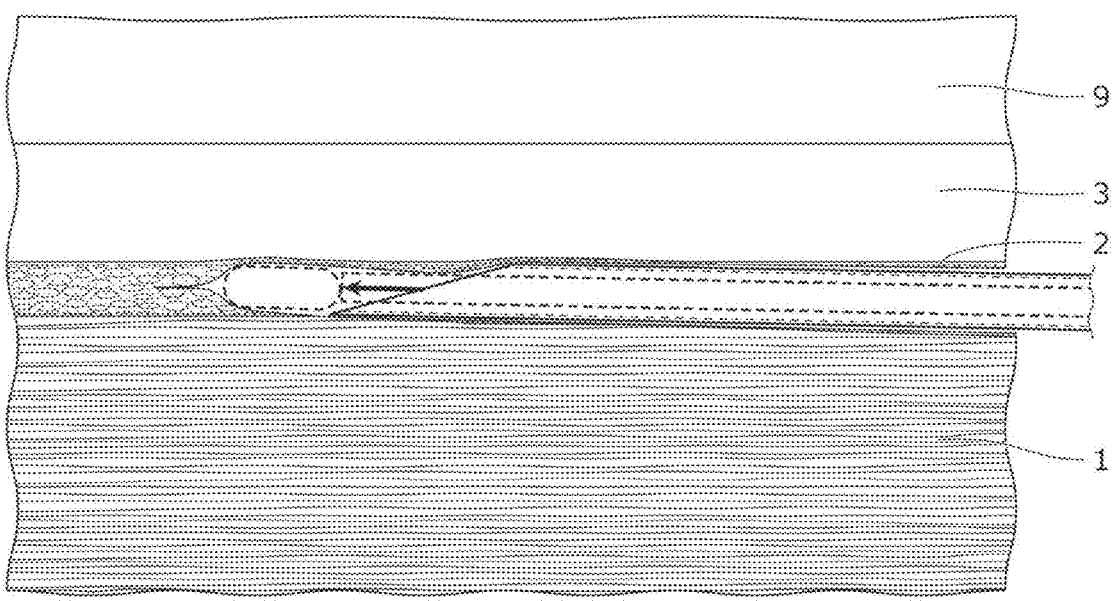
FIG. 8 is an enlarged schematic view illustrating a state in which an implant is inserted into the choroid through a tip opening formed at the tip of an injection needle when implementing the method for placing an implant in the choroid according to the embodiments of the invention.
Figure 9:
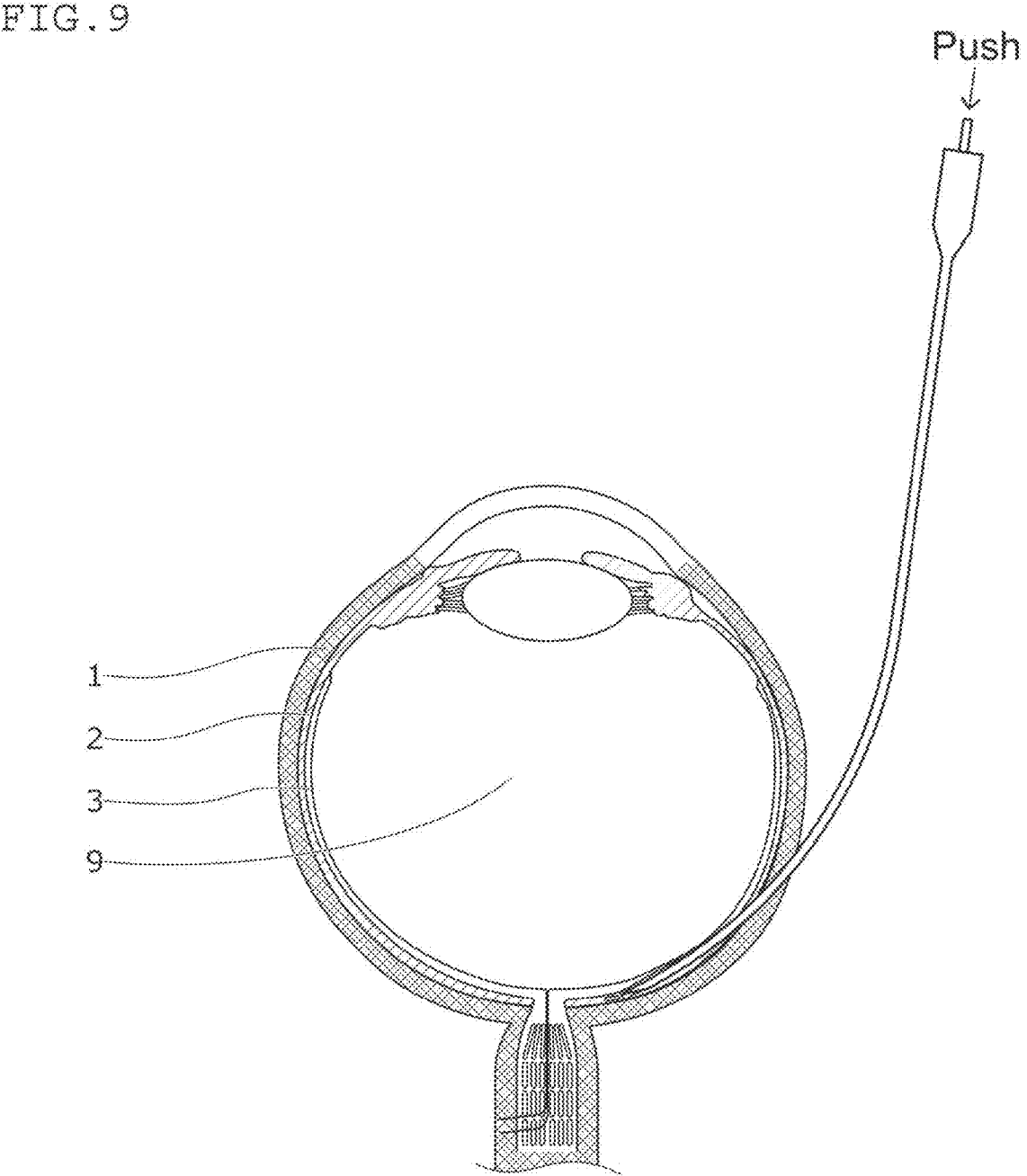
FIG. 9 is a schematic view illustrating a state in which an implant has been inserted into the choroid when implementing the method for placing an implant in the choroid according to the embodiments of the invention.

As illustrated in FIGS. 8 and 9, the implant is inserted into the choroid through the tip opening formed at the tip of the injection needle.

A drug such as a sustained-release dexamethasone preparation may suitably be used as the implant.

It has been reported that a glucocorticoid including dexamethasone has an effect of suppressing inflammation, high-concentration dexamethasone is involved in the activation of anti-inflammatory genes, and low-concentration dexamethasone is involved in the inhibition of inflammatory genes. The intrachoroidal implant that is placed in the choroid using the method according to the embodiments of the invention releases dexamethasone at a high concentration, and then releases dexamethasone at a low concentration (as described later in connection with the examples). This makes it possible to continuously suppress inflammation, and it was demonstrated that experimental uveitis was suppressed for 3 weeks (see Experiment 3).

It has been reported that dexamethasone shows retinal toxicity when administered in an amount of 440 to 4,000 mg. When the method for placing an implant in the choroid according to the embodiments of the invention was used, it was possible to achieve an effective dexamethasone concentration in the retina (posterior eye segment) by placing an implant including only 3 μg of dexamethasone in the choroid, and a serious complication was not observed clinically and histologically (see Example 2).

A drug that includes about 1 mg of dexamethasone is normally used when implementing an intravitreal injection. The method for placing an implant in the choroid according to the embodiments of the invention can achieve the desired effects using a significantly small amount of drug as compared with an intravitreal injection.

It is also preferable to use a tube as the implant. Specifically, it is also preferable to place a tube as the implant in a state in which one end (opening) of the tube is inserted into the choroid. In this case, a drug solution (e.g., anti-inflammatory drug, antibiotic, or antibody preparation) can be injected into the choroid through the tube. This makes it possible to safely and repeatedly inject a drug solution into the choroid in an amount appropriate for the state of a retinal or choroidal disease in the vicinity of the optic disc.

After the drug implant has been placed in the choroid, the injection needle and the plunger are removed from eye, the conjunctiva is sutured, and antibiotic ointment is applied to the eye to complete the surgery. When a tube is used as the implant, the injection needle, the plunger, and a guide wire (inner tube (e.g., 4-0 nylon thread)) are removed from the eye, and the conjunctiva is sutured in a state in which the end (opening) of the tube that is not placed in the choroid is plugged (e.g., with a 1 mm 4-0 nylon thread) and placed under the conjunctiva.

The method for placing an implant in the choroid according to the embodiments of the invention can thus place (insert) the implant in the choroid in the vicinity of the optic disc (see FIG. 9) without performing intraocular surgery.

Figure 10:
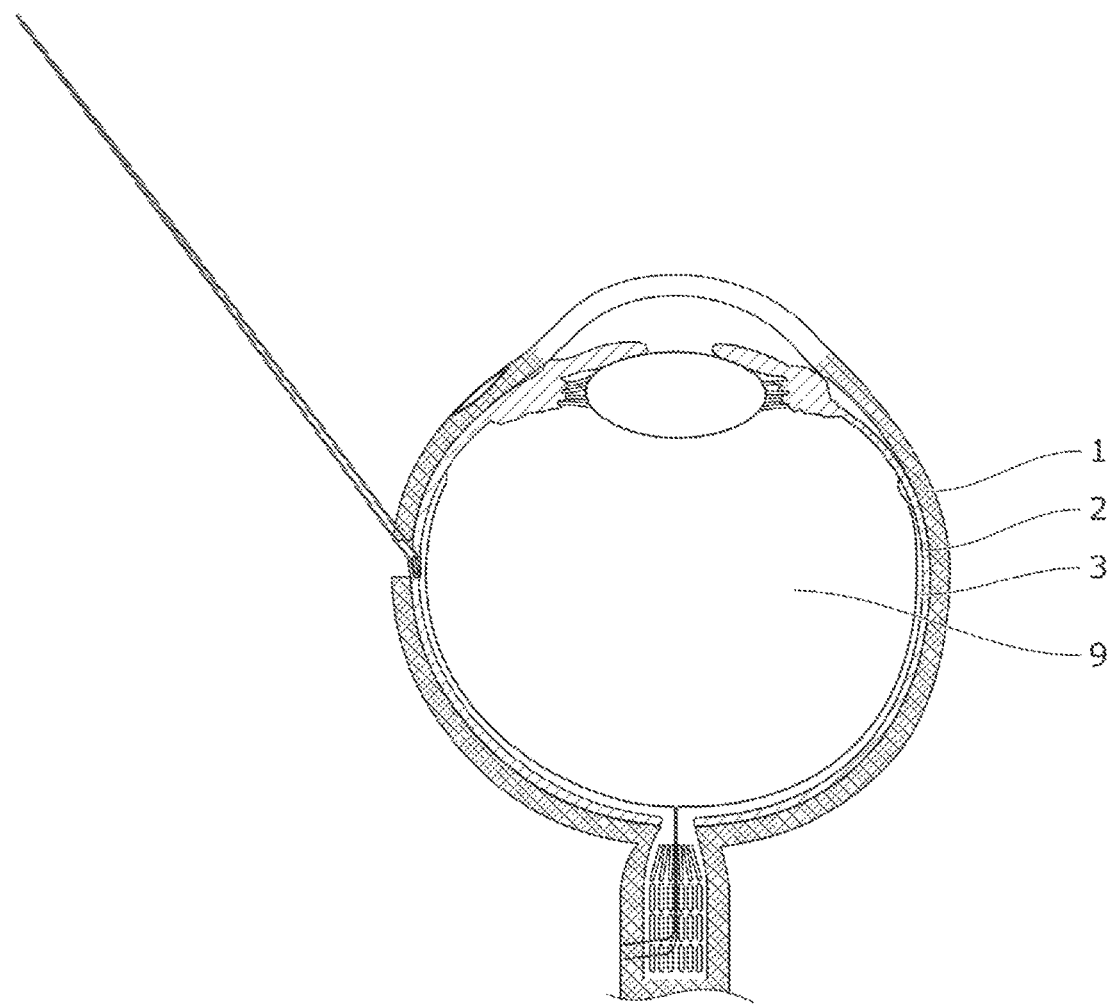
FIG. 10 is a schematic view illustrating a state in which an implant has been inserted into the choroid when implanting a known method for placing an implant in the choroid.

The differences between the known method for placing an implant in the choroid (U.S. Pat. No. 8,349,005) and the method for placing an implant in the choroid according to the embodiments of the invention are described below with reference to FIGS. 9 and 10. FIG. 9 is a view illustrating a state in which an implant is placed (inserted) in the choroid using the method for placing an implant in the choroid according to the embodiments of the invention, and FIG. 10 is a view illustrating a state in which an implant is placed (inserted) in the choroid using the known method for placing an implant in the choroid.

The known method for placing an implant in the choroid can place an implant in the choroid by liquefying the vitreous gel in the eyeball, exposing the choroid, aspirating the vitreous humor to decrease the intravitreous pressure, incising the choroid in the tangential direction, expanding the choroid through bleeding to form a space, and forming a pocket in the choroid. It was impossible to place an implant in the choroid without using the known method for placing an implant in the choroid. According to this method, it is possible to implement relatively safe surgery. Moreover, since the implant is situated close to the retina, it is possible to efficiently deliver a drug to the retina.

Specifically, the known method for placing an implant in the choroid can efficiently deliver a drug to the retina by placing an implant in the choroid.

However, the known method for placing an implant in the choroid has a problem in that the appropriate insertion position of the implant is limited to the equatorial choroid of the eyeball (see FIG. 10), and it is impossible to place an implant in an area of the choroid that is situated within the hemisphere on the side of the posterior eye segment (in particular, an area of the choroid that is situated in the vicinity of the optic disc close to the macular area). This is because the surgical field is narrow, and it is impossible to place a surgical instrument in the posterior eye segment of the eyeball when using the known method for placing an implant in the choroid. Note that FIG. 10 illustrates a state in which an implant is inserted into a pocket formed in the choroid using tweezers.

On the other hand, the method for placing an implant in the choroid according to the embodiments of the invention can insert an implant into the choroid in an area in the vicinity of the optic disc by incising the conjunctiva, inserting a curved injection needle between the conjunctiva and the sclera, advancing the tip of the injection needle to the vicinity of the optic disc along the surface of the sclera, placing a vitrectomy lens over the cornea so that the eyeground can be observed, observing the tip of the injection needle that is seen as an elevated white area in the sclera while observing the eyeground through the vitrectomy lens and pressing the sclera using the tip of the injection needle, moving the tip of the injection needle to determine an appropriate insertion position of the implant in the vicinity of the optic disc, inserting the tip of the injection needle diagonally into the surface of the sclera, and advancing the tip of the injection needle inside the choroid. Therefore, the method for placing an implant in the choroid according to the embodiments of the invention can more efficiently deliver a drug to the posterior eye segment (particularly the vicinity of the optic disc) as compared with the known method for placing an implant in the choroid.

The method for placing an implant in the choroid when a tube is used as the implant is described in detail below with reference to FIGS. 11A and 11B.

Figure 11A:
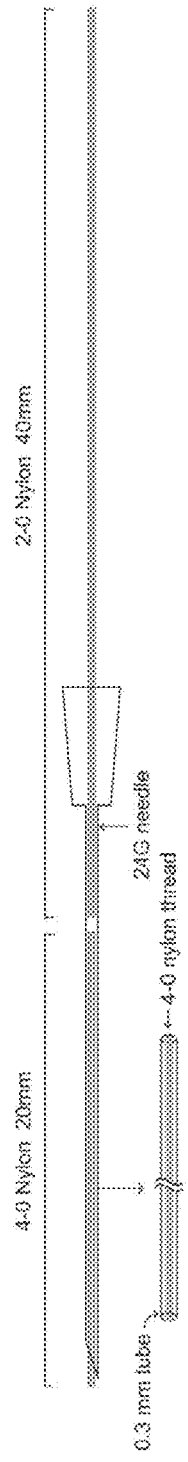
FIG. 11A is a schematic view illustrating an example of an injection needle used when a tube is used as an implant.

FIG. 11A schematically illustrates an example of an injection needle that is used when a tube is placed as the implant (i.e., when a tube is implanted). The injection needle used in connection with the embodiments of the invention is curved as illustrated in FIGS. 2 to 4. FIG. 11A illustrates a state before the injection needle has been curved. FIG. 11B schematically illustrates an example of an implant insertion step.

When a tube is implanted, it is preferable to use a configuration in which a 0.3 mm tube (length: 20 mm, for example) into which a 4-0 nylon thread (length: 20 mm, for example) is inserted, is inserted into an injection needle having a size of 24G, and a 2-0 nylon thread (length: 40 mm, for example) is inserted into the rear end of the injection needle (see FIG. 11A). The 2-0 nylon thread (that serves as a plunger) is used to push the tube (that serves as an implant) toward the outside through the tip of the injection needle. The 4-0 nylon thread serves as a guide wire (inner rod) for inserting the tube into the choroid while supporting the tube.

In the implant insertion step, the tip of the injection needle is advanced inside the choroid parallel to the choroid using the method for placing an implant in the choroid according to the embodiments of the invention to insert the tip opening of the injection needle into the choroid. The 2-0 nylon thread is pushed with the right hand while fixing the injection needle with the left hand using tweezers or the like to insert the tube (and the 4-0 nylon thread) into the choroid through the tip of the injection needle (see I in FIG. 11B).

Figure 11B:
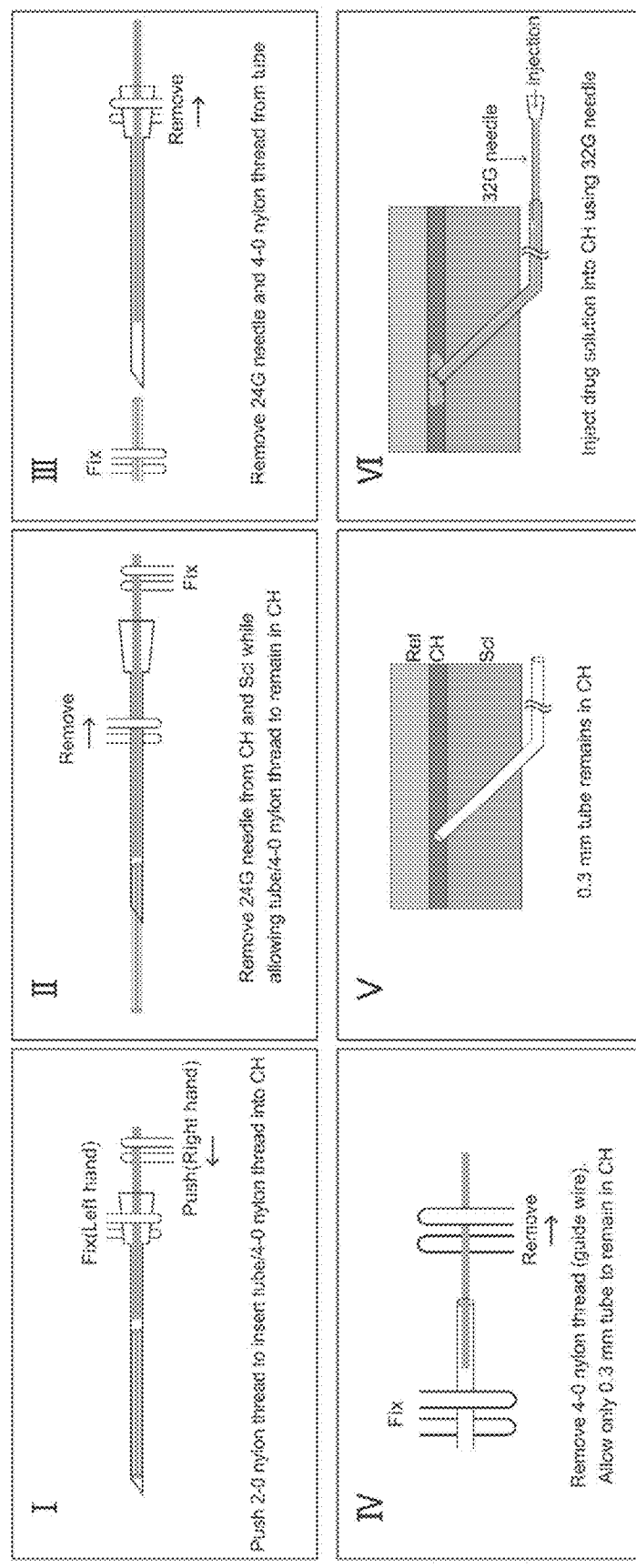
FIG. 11B is a schematic view illustrating an example of an implant insertion step when a tube is used as an implant, when implementing the method for placing an implant in the choroid according to the embodiments of the invention.

The injection needle is removed from the choroid and the sclera while fixing the plunger (2-0 nylon thread) so that the tube (and the 4-0 nylon thread) remains in the choroid (see II in FIG. 11B). The injection needle is removed from the tube together with the 2-0 nylon thread while fixing the tube so that the tube (and the 4-0 nylon thread) remains in the choroid (see III in FIG. 11B).

The 4-0 nylon thread (guide wire) is removed from the tube while fixing the tube so that only the tube remains in the choroid (see IV and V in FIG. 11B). As a result, one end of the tube opens within the choroid, and the other end of the tube opens in the vicinity of the incised conjunctiva. The end of the tube is inserted into the choroid in a state in which the main body of the tube extends between the conjunctiva and the sclera from the vicinity of the incised conjunctiva, and passes through the sclera in the vicinity of the optic disc.

An injection needle having a size of 32G is inserted into the tip opening of the tube situated in the vicinity of the conjunctiva, and a drug solution is injected into the choroid through the injection needle having a size of 32G (see VI in FIG. 11B).

Figure 12:
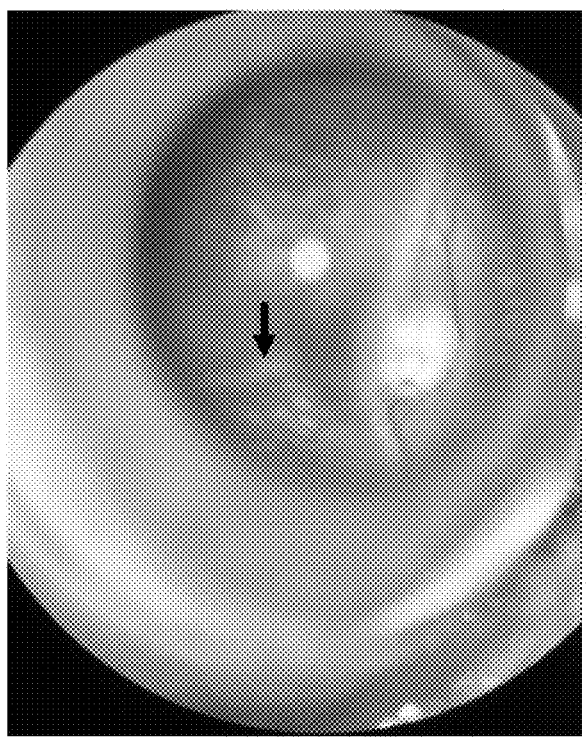
FIG. 12 is a view illustrating a fundus photograph in a state in which a tube used as an implant has been inserted into the choroid, when implementing the method for placing an implant in the choroid according to the embodiments of the invention.

FIG. 12 illustrates a fundus photograph in a state in which a tube is inserted into the choroid. In FIG. 12, the arrow indicates a tube inserted into the choroid, and a drug (that is colored using indocyanine green in the example illustrated in FIG. 12) is released from the tube toward the optic disc (that is indicated by the white circle in FIG. 12 (see the lower part)).

When a tube is used as the implant as described above when implementing the method for placing an implant in the choroid according to the embodiments of the invention, it is possible to repeatedly inject a drug solution into the choroid at an arbitrary timing in an amount appropriate for the state of a retinal disease. Since the drug can be repeatedly injected through the tube, the amount of drug can be adjusted (i.e., increased or decreased) taking account of the state of the disease, and it is possible to administer the drug at the effective dose for a long time.

It is also preferable to provide a valve outside the tube (e.g., at the end of the tube). When a valve is provided to the tube, it is possible to prevent a situation in which the tube is easily removed from the choroid. Such a valve may be formed by diagonally forming one shallow cut or a plurality of shallow cuts in the outer wall surface of the end of the tube from the rear side, for example. It is possible to prevent the backward flow of the drug solution by providing a valve inside the tube.

It is also possible to facilitate observation of the state of the tube during eyeground observation by putting a graded scale on the tube and/or coloring the tube. A micropump may be connected to the sclera-side end of the tube so that a drug can be released in a sustained manner.

Furthermore, it may be useful to cover the scleral side end of tube by contact lens or silicone plate or the like for fixing the tube and avoiding infections.

Tool for Placing Implant in Choroid

A tool for placing an implant in the choroid that is used when implementing the method for placing an implant in the choroid according to the embodiments of the invention is described below.

A tool for placing an implant in the choroid according to the embodiments of the invention includes: an injection needle that includes a main body that includes a tip having a tip opening at one end, and is hollow and curved, and a support that supports the main body; and a plunger that is inserted into the main body, and pushes the implant forward through the tip opening. The tool may further include an injector that moves the plunger inside the main body of the injection needle.

Specifically, the injection needle having a size of 24G illustrated in FIGS. 11A and 11B corresponds to the injection needle included in the tool, the 2-0 nylon thread corresponds to the plunger included in the tool, and the tube corresponds to the implant that is placed using the tool. Note that a drug may be used as the implant that is placed using the tool.

FIGS. 13A to 13D illustrate a specific example of the tool for placing an implant in the choroid according to the embodiments of the invention. In the specific example illustrated in FIGS. 13A to 13D, a drug is used as the implant.

FIG. 13A illustrates the implant that is inserted into the choroid using the injection needle. The implant is a sustained-release dexamethasone preparation prepared by mixing dexamethasone and polylactic acid.

FIG. 13B illustrates the injection needle. The arrow indicates the plunger that is inserted into the injection needle.

FIG. 13C illustrates the tip of the injection needle. The arrow indicates the plunger, and the triangle indicates the implant that has been pushed forward by the plunger through the tip opening formed at the tip of the injection needle.

FIG. 13D illustrates the injector and the injection needle loaded into the injector. When a button indicated by the arrow is pressed, the plunger gradually moves inside the needle toward the tip of the injection needle. The implant is thus pushed by the plunger inside the needle, and discharged through the tip of the injection needle. The injector is a pen-type electric dispenser manufactured by ICOMES LAB Co. Ltd.

It is preferable to use nylon as a material for forming the plunger, for example. When a wire is used as the plunger, it may be difficult to push the plunger along the curved injection needle since the plunger may be caught within the curved injection needle due to too high a hardness. When a silk thread is used as the plunger, the plunger can be pushed along the curved injection needle, but it may be difficult to push the implant forward due to too high a softness. Since nylon has moderate hardness and elasticity, nylon is suitable as the material for forming the plunger. Note that the material for forming the plunger is not particularly limited to nylon. A material having a hardness similar to that of nylon may also suitably be used.

When the tool for placing an implant in the choroid according to the embodiments of the invention is used, it is possible to insert the injection needle through the incised part of the conjunctiva, move the injection needle along the sclera, and less invasively and simply place the implant in the choroid in the vicinity of the optic disc (see FIGS. 2 to 9).

EXAMPLES

Experiment 1

Experiments were performed to determine the drug release effect of an intrachoroidal implant, an intravitreal implant, and an intrascleral implant. In Experiment 1, the implant was placed in the choroid using the known method illustrated in FIG. 10. Specifically, the implant can be placed in the choroid in the vicinity of the optic disc using the method for placing an implant in the choroid according to the embodiments of the invention, but it is impossible to place the implant in the sclera in the vicinity of the optic disc using the method for placing an implant in the choroid according to the embodiments of the invention. Therefore, the implant was placed in the choroid using the known method in order to compare the intravitreal implant, the intrascleral implant, and the intrachoroidal implant as to the drug release effect.

Gelatin was cut to have a size of 0.3 (length)×0.3 (width)×0.1 (thick) mm. After injecting 3 µg of dexamethasone into the gelatin, the gelatin was dried to obtain an implant (gelatin implant).

Twelve 3-month-old Japanese white rabbits (purchased from Japan SLC, Inc., weight: 2 to 2.5 kg) were used as subjects. The rabbits were equally divided into an intrachoroidal implant group, an intravitreal implant group, and an intrascleral implant group, and the implant was placed in one of the eyes of each rabbit belonging to each group.

Regarding the intrachoroidal implant group, the vitreous gel in the eyeball was liquefied, and the implant was placed in the choroid using the known method for placing an implant in the choroid. The implant was placed in the choroid at a position 6 mm below the cornea.

Regarding the intravitreal implant group, the implant was placed in the vitreous body at a position 2 mm above the cornea.

Regarding the intrascleral implant group, the implant was placed in the sclera at a position 6 mm below the cornea.

Figure 14:
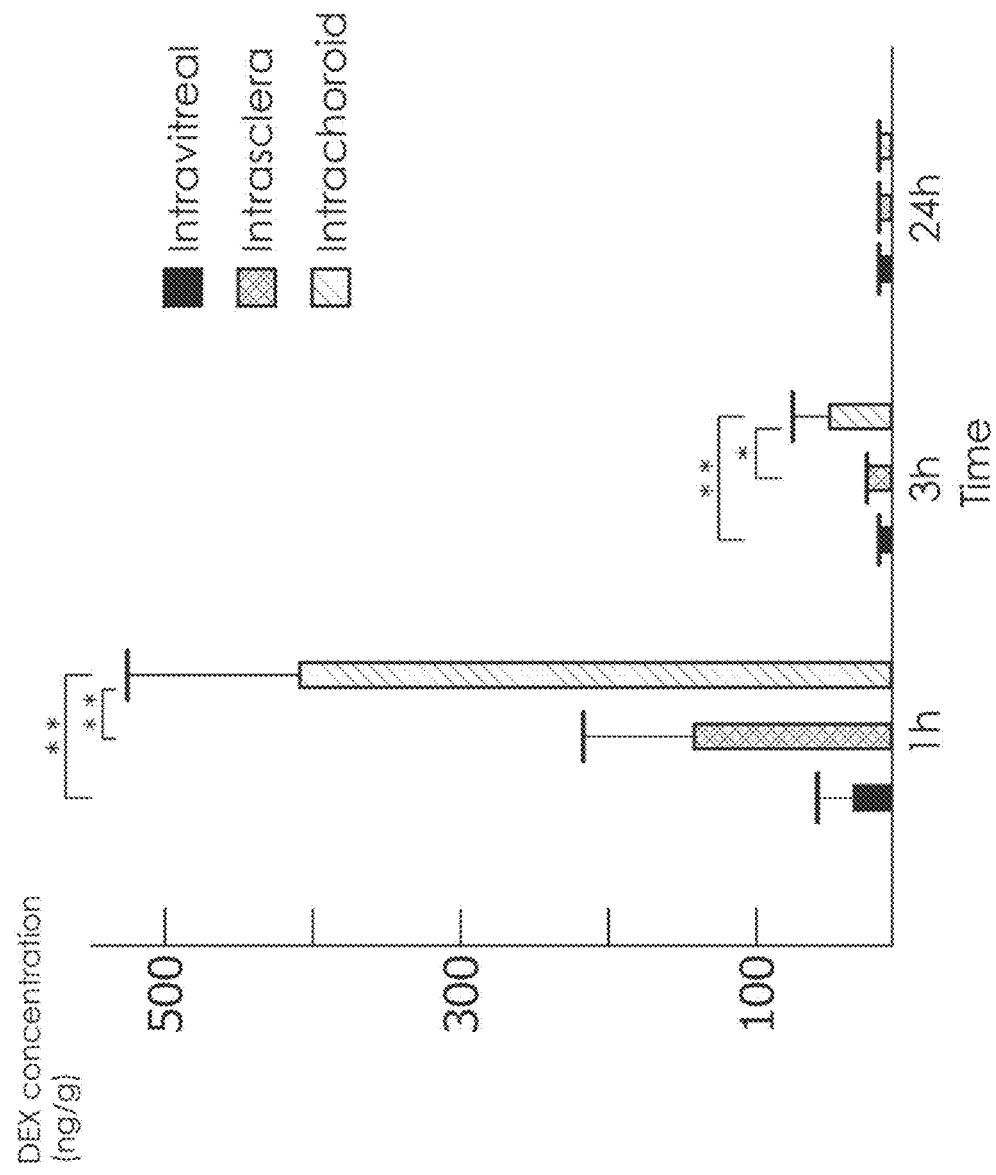
FIG. 14 is a view illustrating a graph of the experimental results for the release of a drug when an intravitreal implant, an intrascleral implant, or an intrachoroidal implant was used (Note: The implant was placed in the choroid using the known method illustrated in FIG. 10. Specifically, the implant can be placed in the choroid in the vicinity of the optic disc using the method for placing an implant in the choroid according to the embodiments of the invention, but it is impossible to place the implant in the sclera in the vicinity of the optic disc using the method for placing an implant in the choroid according to the embodiments of the invention. Therefore, the implant was placed in the choroid using the known method in order to compare the intravitreal implant, the intrascleral implant, and the intrachoroidal implant as to the drug release effect).

The eyeball was removed from each rabbit (four rabbits) belonging to each group when 1, 3, and 24 hours had elapsed after the placement of the implant. The inferior retina (10×10 mm) was removed from the posterior eye segment, and the dexamethasone concentration in the retina was measured by liquid chromatography/mass spectrometry/mass spectrometry (LC/MS/MS) using a mass spectrometer (manufactured by AB SCIEX). The results are shown in FIG. 14. In FIG. 14, the symbol "*" indicates P<0.05, and the symbol "**" indicates P<0.01.

As shown in FIG. 14, the dexamethasone concentration in the retina of the intravitreal implant group when 1, 3, and 24 hours had elapsed after the placement of the implant was 13.5±8.7 ng/g, 3.6±4.2 ng/g, and 4.2±4.5 ng/g, respectively (number of samples: 4, mean±SD).

The dexamethasone concentration in the retina of the intrascleral implant group when 1, 3, and 24 hours had elapsed after the placement of the implant was 122.5±79.7 ng/g, 5.4±4.0 ng/g, and 3.3±3.2 ng/g, respectively (number of samples: 4, mean±SD).

The dexamethasone concentration in the retina of the intrachoroidal implant group when 1, 3, and 24 hours had elapsed after the placement of the implant was 408.8±115.3 ng/g, 23.8±10.2 ng/g, and 4.7±3.3 ng/g, respectively (number of samples: 4, mean±SD).

It was thus confirmed that the dexamethasone concentration in the retina of the intrachoroidal implant group was significantly higher than the dexamethasone concentration in the retina of the intravitreal implant group and of the intrascleral implant group when 1 and 3 hours had elapsed after the placement of the implant, and the intrachoroidal implant could effectively deliver dexamethasone to the posterior eye segment.

Specifically, the intrachoroidal implant that was placed using the known method could more effectively deliver the drug to the posterior eye segment as compared with the intravitreal implant and the intrascleral implant.

Experiments 2 and 3 (see below) were performed to determine the effects of the method for safely and simply placing an implant in the choroid in the vicinity of the optic disc according to the embodiments of the invention.

Experiment 2

The following experiment was performed to determine the effects of the method for placing an implant in the choroid according to the embodiments of the invention.

Seventy-five (75) mg of polylactic acid (PLA) (manufactured by Wako Pure Chemical Industries, Ltd.) and 25 mg of dexamethasone (manufactured by Sigma) were mixed, and the mixture was freeze-dried at −80° C. for 48 hours. The resulting composition was pressed and cut to prepare a rod-like implant (weight: 12 µg, width: 0.2 mm, thickness: 0.2 mm, length: 1.0 mm) containing 25 wt % of dexamethasone (DEX-PLA implant). The dexamethasone content in the implant was 3 µg.

Nine 3-month-old Japanese white rabbits (purchased from Japan SLC, Inc., weight: 2 to 2.5 kg) were used as subjects, and the implant was placed in one of the eyes of each rabbit.

The implant was placed in the choroid using the method for placing an implant in the choroid according to the embodiments of the invention. Specifically, the conjunctiva was incised, and an injection needle having a size of 25G was inserted between the conjunctiva and the sclera. The tip of the injection needle was advanced to the vicinity of the optic disc along the surface of the sclera. After placing a vitrectomy lens over the cornea so that the eyeground could be observed, the tip of the injection needle appearing white was observed while observing the eyeground through the vitrectomy lens and pressing the sclera using the tip of the injection needle. The tip of the injection needle was moved to determine an appropriate insertion position of the implant in the vicinity of the optic disc, and the tip of the injection needle was inserted diagonally into the sclera. The tip of the injection needle was advanced into the choroid, and the implant was inserted into the choroid through the tip opening formed at the tip of the injection needle.

Figure 15B:
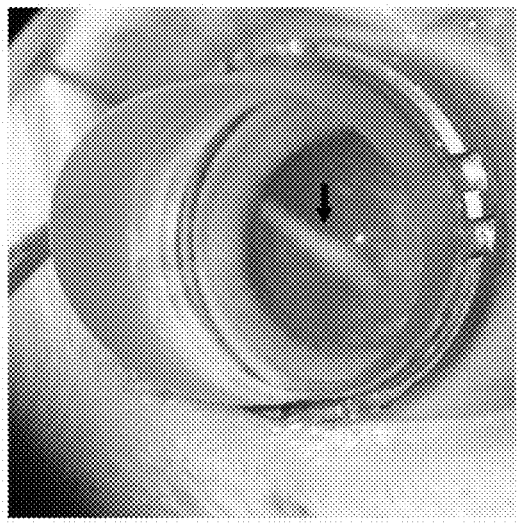
FIG. 15B is a view (photograph) illustrating a state in which the tip of an injection needle has been advanced to the vicinity of the optic disc, a vitrectomy lens has been placed over the cornea so that the eyeground can be observed, and the tip of the injection needle appearing white is observed while observing the eyeground through the vitrectomy lens and pressing the sclera using the tip of the injection needle in order to determine the placement position of the implant.
Figure 15D:
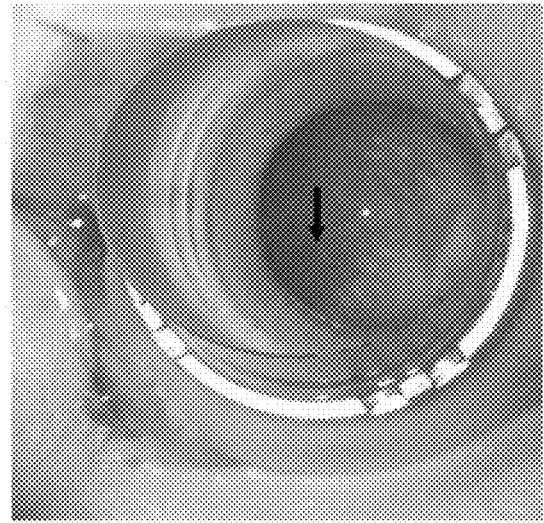
FIG. 15D is a view (photograph) illustrating a state in which the implant has been inserted into the choroid through the tip of the injection needle using the plunger.
Figure 15A:
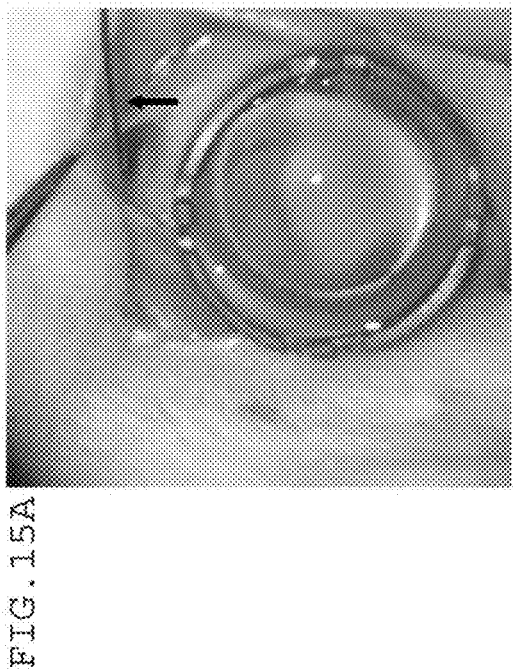
FIG. 15A is a view (photograph) illustrating a state in which the conjunctiva is incised, and an injection needle is inserted between the conjunctiva and the sclera when implementing the method for placing an implant in the choroid according to the embodiments of the invention.

FIG. 15A illustrates a state in which the conjunctiva was incised, and an injection needle (see the arrow) having a size of 25G was inserted between the conjunctiva and the sclera.

FIG. 15B illustrates a state in which the tip of the injection needle was advanced to the vicinity of the optic disc, the vitrectomy lens was placed over the cornea, and the tip of the injection needle appearing white through the vitrectomy lens was observed while pressing the sclera using the tip of the injection needle (see the arrow) in order to determine the placement position of the implant.

Figure 15C:
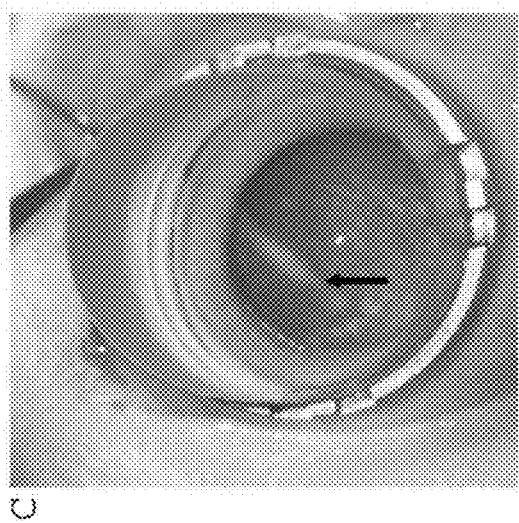
FIG. 15C is a view (photograph) illustrating a state in which the tip of the injection needle is inserted into the choroid.

FIG. 15C illustrates a state in which the tip of the injection needle having a size of 25G (see the arrow) was inserted into the choroid.

FIG. 15D illustrates a state in which the implant (see the arrow) was inserted into the choroid through the tip of the injection needle using the plunger.

The eyeball was removed from each rabbit (three rabbits) belonging to each group when 24 hours, 1 week, and 3 weeks had elapsed after the placement of the implant. The inferior retina (5×5 mm) was removed from the posterior eye segment, and the dexamethasone concentration in the retina was measured by LC/MS/MS using a mass spectrometer (manufactured by AB SCIEX). The results are shown in FIG. 16.

Figure 16:
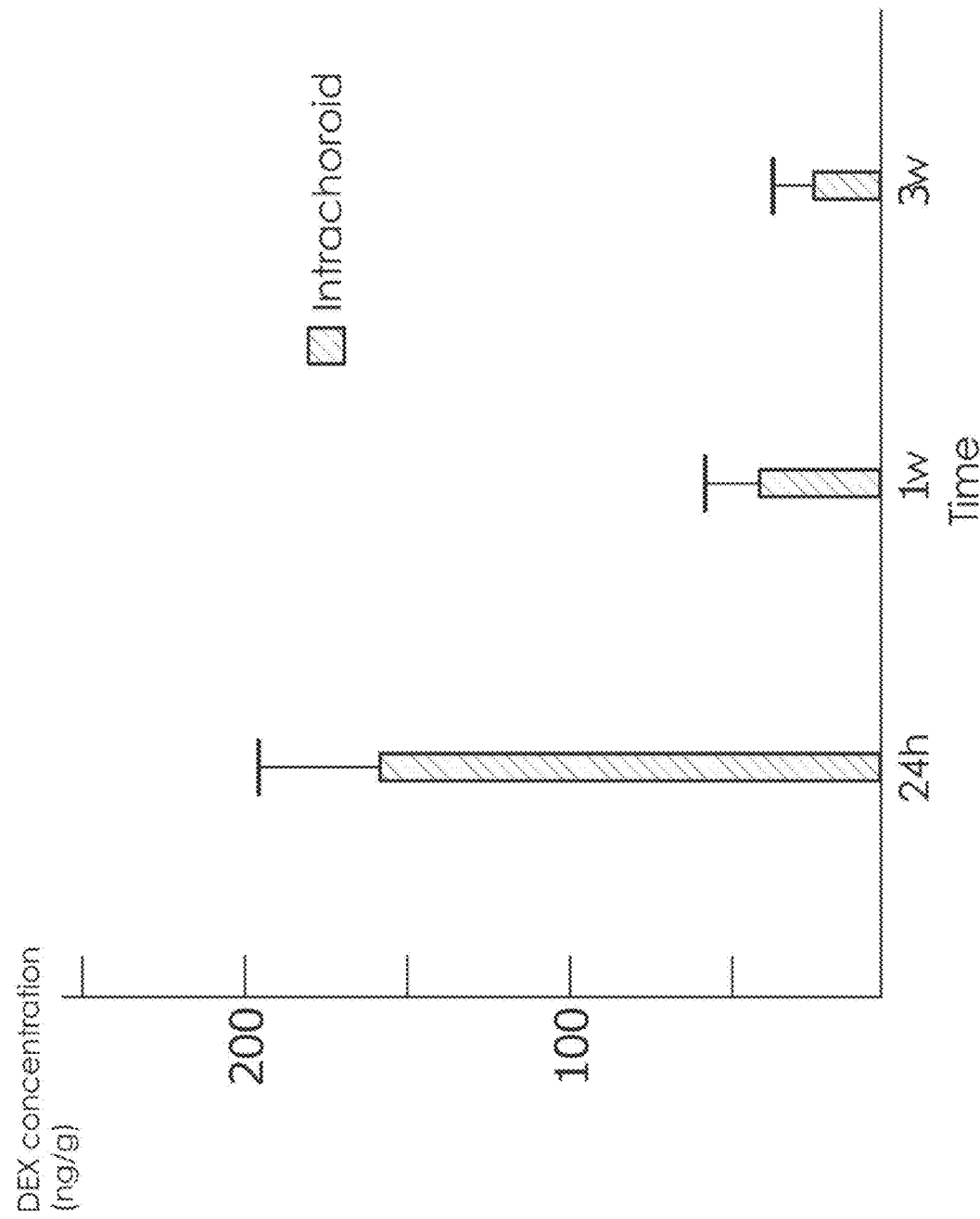
FIG. 16 is a view illustrating a graph of the experimental results for the release of a drug when an implant was placed in the choroid using the method for placing an implant in the choroid according to the embodiments of the invention.

As shown in FIG. 16, the dexamethasone concentration in the retina when 24 hours, 1 week, and 3 weeks had elapsed after the placement of the implant was 159.0±28.2 ng/g, 41.2±14.2 ng/g, and 17.2±11.3 ng/g, respectively (number of samples: 3, mean±SD). It is known that the effective dexamethasone concentration in the retina is 0.15 to 4 µg/ml (150 to 4,000 ng/g). Specifically, the effective dexamethasone concentration was obtained when 24 hours had elapsed after the placement of the implant, and constant suspended release of dexamethasone was observed when 1 week and 3 weeks had elapsed after the placement of the implant.

The eyeground of each rabbit (three rabbits) belonging to each group was observed before removing the eyeball when 24 hours, 1 week, and 3 weeks had elapsed after the placement of the implant, and histological examination was performed on the removed eyeball when 3 weeks had elapsed after the placement of the implant. The results are shown in FIGS. 17A and 17B.

Figure 17B:
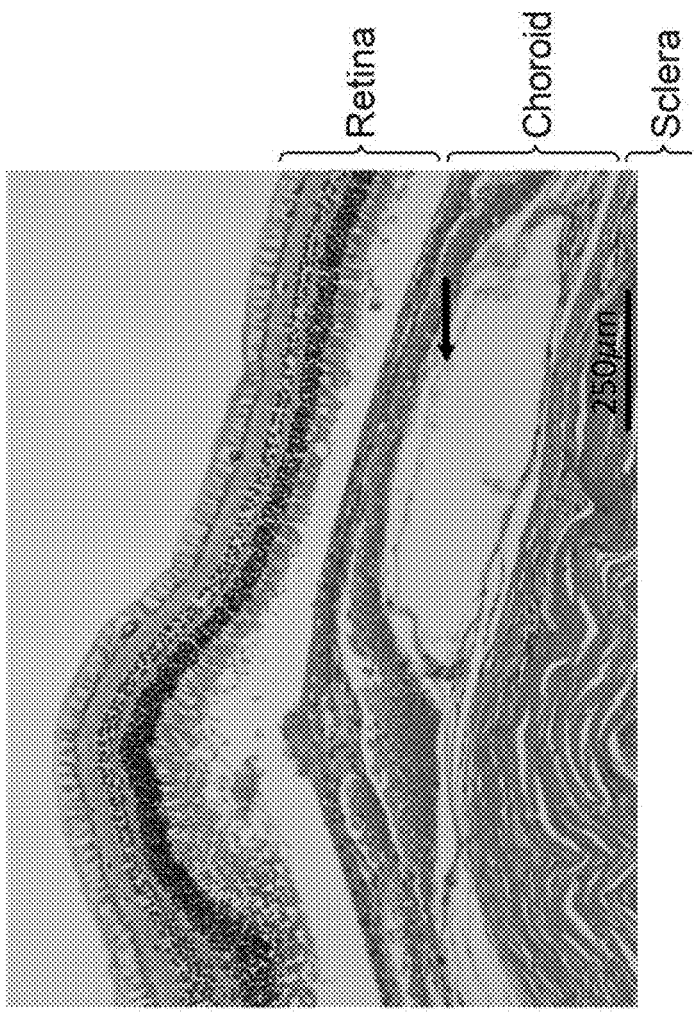
FIG. 17B is a view illustrating a histological photograph when 3 weeks had elapsed after an implant was placed in the choroid using the method for placing an implant in the choroid according to the embodiments of the invention.
Figure 17A:
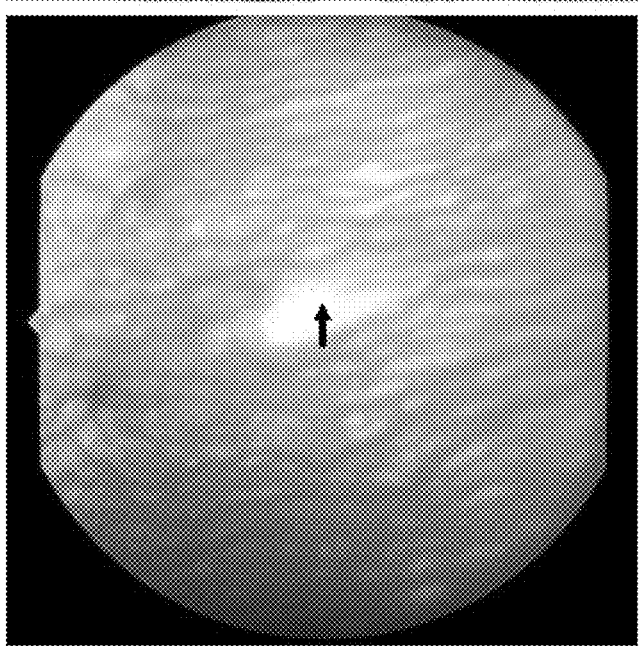
FIG. 17A is a view illustrating a fundus photograph when 3 weeks had elapsed after an implant was placed in the choroid using the method for placing an implant in the choroid according to the embodiments of the invention.

As shown in FIGS. 17A and 17B, a white lesion was observed at a position at which the intrachoroidal implant was placed when the eyeground was observed when 3 weeks had elapsed after the placement of the implant, but no abnormalities were observed in the remaining area.

Abnormalities were observed histologically in the photoreceptor outer segment and the outer nuclear layer when 3 weeks had elapsed after the placement of the implant at a position at which the intrachoroidal implant was placed, but no abnormalities were observed in the remaining area.

These results suggest that the white lesion observed at a position at which the intrachoroidal implant was placed, and the abnormalities observed in the photoreceptor outer segment and the outer nuclear layer at a position at which the intrachoroidal implant was placed, were not serious tissue injury, and the method for placing an implant in the choroid according to the embodiments of the invention can be implemented safely.

Experiment 3

The following experiment was performed to determine the uveitis suppression effect of the intrachoroidal implant placed using the method for placing an implant in the choroid according to the embodiments of the invention.

Note that experimental uveitis is not completely identical to clinical uveitis, but is similar to clinical uveitis as to the acute stage, and the suppression of ocular inflammation is achieved as a result of the suppression of vascular and cellular inflammation.

Eight 3-month-old Japanese white rabbits (purchased from Japan SLC, Inc., weight: 2 to 2.5 kg) were used as subjects. The rabbits were equally divided into a group in which a dexamethasone-containing polylactic acid (DEX-PLA) implant was placed in the choroid using the method for placing an implant in the choroid according to the embodiments of the invention, and a group in which a PLA implant (control) (that did not contain dexamethasone) was placed in the choroid.

One hundred (100) ng of lipopolysaccharide was injected into the vitreous of each rabbit to induce experimental uveitis, and the posterior eye segment of each rabbit was histologically examined when 3 weeks had elapsed. Note that the implant was prepared and placed in the same manner as described above in connection with Experiment 2. The results are shown in FIGS. 18A and 18B.

Figure 18A:
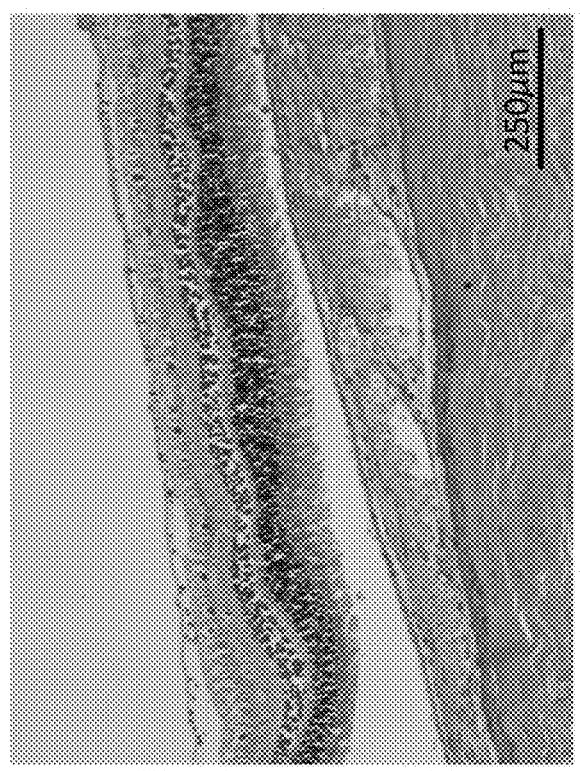
FIG. 18A is a view illustrating a histological photograph of a control.
Figure 18B:
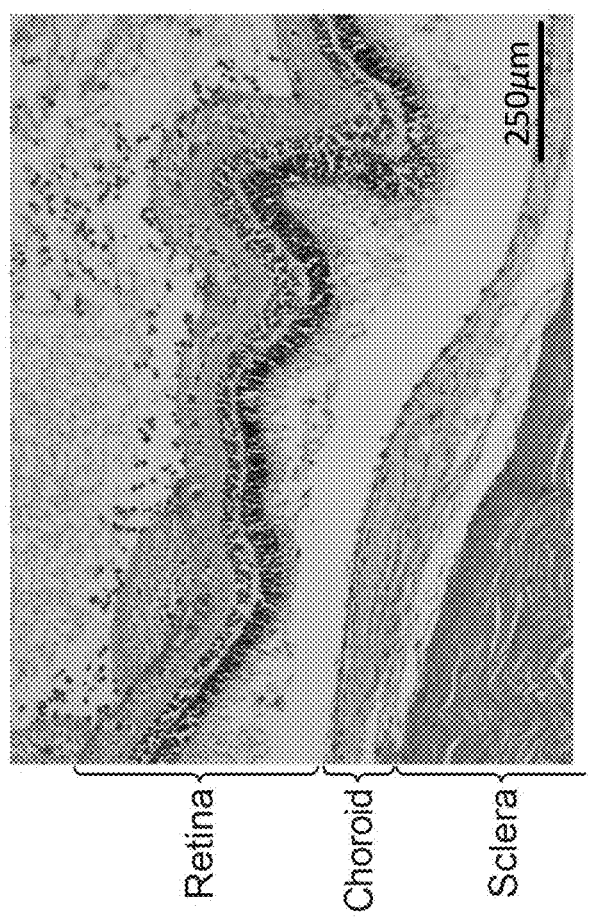
FIG. 18B is a view illustrating a histological photograph when 3 weeks had elapsed after experimental uveitis was induced after the placement of an implant in the choroid using the method for placing an implant in the choroid according to the embodiments of the invention.

As shown in FIG. 18A, an inflammatory change was observed in the vitreous body and the surface layer of the retina when the posterior eye segment of the rabbit belonging to the control implant group was observed. As shown in FIG. 18B, an inflammatory change was suppressed in the posterior eye segment of the rabbit belonging to the DEX-PLA implant group.

It was thus confirmed that the method for placing an implant in the choroid according to the embodiments of the invention can place an implant in the choroid in the vicinity of the optic disc.

It was also confirmed that the effective dexamethasone concentration in the retina in the posterior eye segment can be achieved (determined), serious tissue injury can be inhibited, and experimental uveitis can be suppressed when the intrachoroidal implant described above in connection with the embodiments of the invention is used.

The invention is not limited to the above embodiments and examples. Various modifications may be made without departing from the scope of the invention.

For example, when a tube is used as the implant (instead of a solid drug (see the examples)), a liquid or jelly-like drug or the like can be repeatedly injected into the choroid through the tube, and it is possible to maintain the effective drug concentration in the retina in the posterior eye segment (particularly in an area from the optic disc to the macula). The material to be implanted, and the material to be injected through the tube may be appropriately changed.

INDUSTRIAL APPLICABILITY

The invention may suitably be used when placing an implant that includes a drug in the choroid of a human, a pet, or the like, and releasing the drug within the eye in a sustained manner for a long time to treat retinal/choroidal/vitreous diseases and the like, or when placing an implant that includes vascular endothelial growth factor (VEGF), a fibroblast growth factor, or the like in the choroid of an experimental animal (e.g., rabbit) to provide a model animal used for a clinical trial, for example. In particular, the invention may suitably be used to less invasively and simply place an implant in the choroid in the vicinity of the optic disc.

The documents described in the specification are incorporated herein by reference in their entirety.

REFERENCE SIGNS LIST

1 Sclera
2 Choroid
3 Retina
4 Cornea
5 Iris
6 Ciliary body
7 Zonule of Zinn
8 Crystalline lens
9 Vitreous body
10 Aqueous humor

What is claimed is:

1. A method for placing an implant in a choroid that can less invasively and simply place the implant in the choroid in an optic disc-macula area, the method comprising
   incising a conjunctiva,
   inserting an injection needle between the conjunctiva and a sclera,
   advancing a tip of the injection needle to a vicinity of an optic disc along a surface of the sclera,
   placing a vitrectomy lens over a cornea so that an eyeground can be observed,
   observing the tip of the injection needle that is seen as an elevated white area in the sclera while observing the eyeground through the vitrectomy lens and pressing the sclera using the tip of the injection needle,
   moving the tip of the injection needle to determine an appropriate insertion position of the implant in the vicinity of the optic disc,
   inserting the tip of the injection needle diagonally into the sclera,
   advancing the tip of the injection needle into the choroid, and
   inserting the implant into the choroid in the optic disc-macula area through a tip opening formed at the tip of the injection needle.

2. The method according to claim 1, further comprising:
   determining that the tip of the injection needle has been inserted into the choroid through the vitrectomy lens after inserting the tip of the injection needle diagonally into the sclera, advancing the tip of the injection needle within the choroid parallel to the choroid until it is observed through the vitrectomy lens that the tip opening of the injection needle has been inserted into the choroid, and
   inserting the implant into the choroid.

3. The method according to claim 2, wherein the determining that the tip of the injection needle has been inserted into the choroid comprises determining that the tip of the injection needle has been inserted into the choroid when a state in which the tip of the injection needle is observed through a thick membrane comprising the retina, the choroid, and the sclera has changed to a state in which the tip of the injection needle is observed through a thin membrane comprising the retina and the choroid when the eyeground is observed through the vitrectomy lens.

4. The method according to claim 1, wherein the moving the tip of the injection needle to determine the appropriate insertion position of the implant comprises
   observing the tip of the injection needle that is seen as the elevated white area in the sclera through the vitrectomy lens from a side of the retina while pressing the sclera using the tip of the injection needle, and
   determining the surface of the sclera that is contiguous to an area of the choroid in the vicinity of the optic disc in which a number of blood vessels is small, to be the insertion position of the implant.

5. The method according to claim 1, wherein an implant that comprises an anti-inflammatory drug, an antibiotic, or an antibody is inserted as the implant.

6. The method according to claim 1, further comprising:
   inserting a tube into the choroid as the implant,
   allowing one end of the tube to remain in the choroid, and
   repeatedly injecting a drug solution comprising an anti-inflammatory drug, an antibiotic, or an antibody into the choroid through the tube while adjusting an amount of the drug solution taking account of a state of a disease.

* * * * *